(12) United States Patent
Kennedy

(10) Patent No.: US 9,301,856 B2
(45) Date of Patent: Apr. 5, 2016

(54) SEPARATION OF HIP JOINT LINER AND SOCKET ELEMENTS

(76) Inventor: Michael T. Kennedy, San Clemente, CA (US)

(*) Notice: Subject to any disclaimer, the term of this patent is extended or adjusted under 35 U.S.C. 154(b) by 0 days.

(21) Appl. No.: 13/573,116

(22) Filed: Aug. 23, 2012

(65) Prior Publication Data
US 2015/0351932 A1 Dec. 10, 2015

(51) Int. Cl.
*A61F 2/46* (2006.01)

(52) U.S. Cl.
CPC .............. *A61F 2/4637* (2013.01); *A61F 2/4609* (2013.01); *A61F 2002/4619* (2013.01); *A61F 2002/4641* (2013.01)

(58) Field of Classification Search
CPC .. A61F 2/34; A61F 2/4609; A61F 2002/4629
USPC ................................. 606/81, 91, 99
See application file for complete search history.

(56) References Cited

U.S. PATENT DOCUMENTS

| 4,878,918 A * | 11/1989 | Tari et al. .................... 623/22.35 |
| 2007/0005144 A1* | 1/2007 | Leisinger .............. A61F 2/4637 623/22.29 |
| 2010/0131073 A1* | 5/2010 | Meridew ................... A61F 2/34 623/22.28 |
| 2011/0224742 A1* | 9/2011 | Weisel et al. ................ 606/86 R |

* cited by examiner

*Primary Examiner* — Samuel Hanna
(74) *Attorney, Agent, or Firm* — William W. Haefliger

(57) ABSTRACT

An apparatus and a method for removing a hip socket liner from surface attachment to a socket, that includes providing a carrier and multiple penetrators carried to be displaced relative to the carrier, inserting the carrier in the liner so that the penetrators project toward a liner cup-shaped surface, effecting controlling limited forceful displacement of tips defined by the penetrators toward and into said liner cup-shaped surface, and transmitting pushing force acting between the carrier and hip socket whereby the liner is suddenly freed from attachment to the socket.

5 Claims, 3 Drawing Sheets

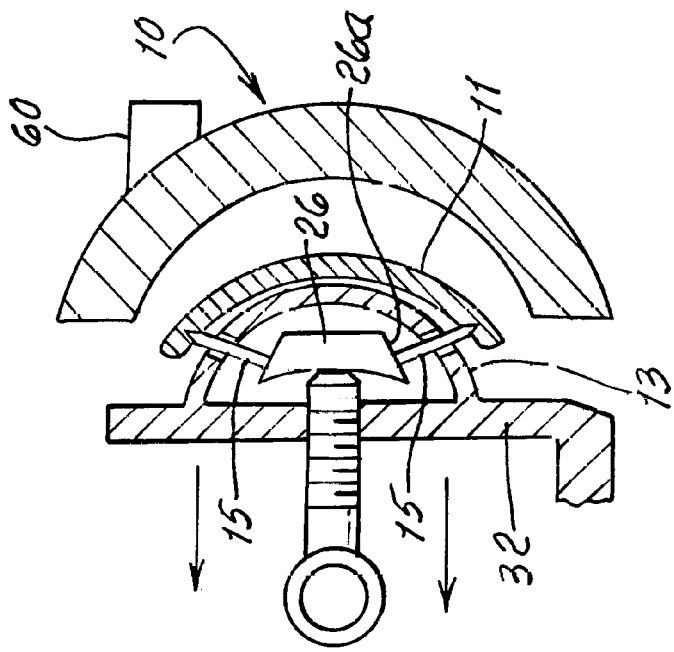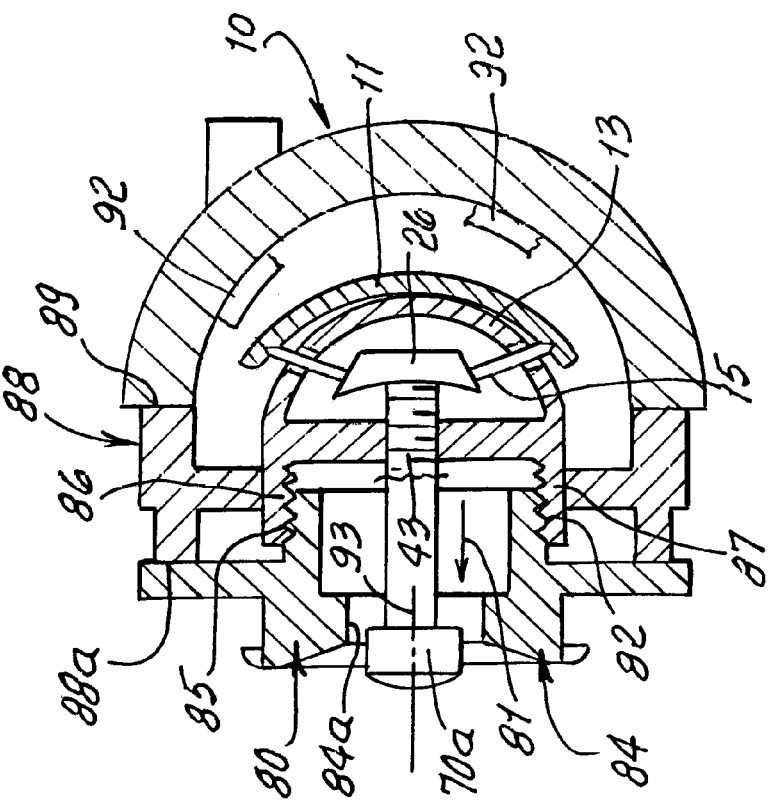

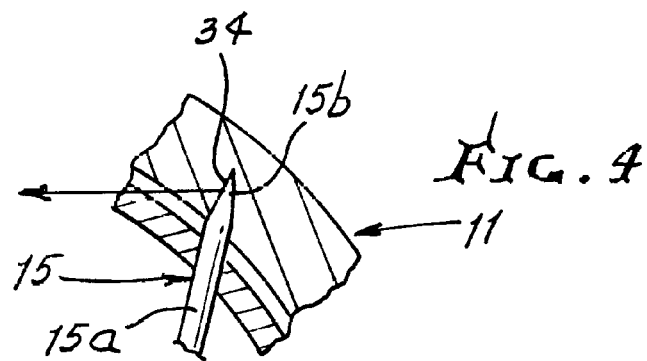
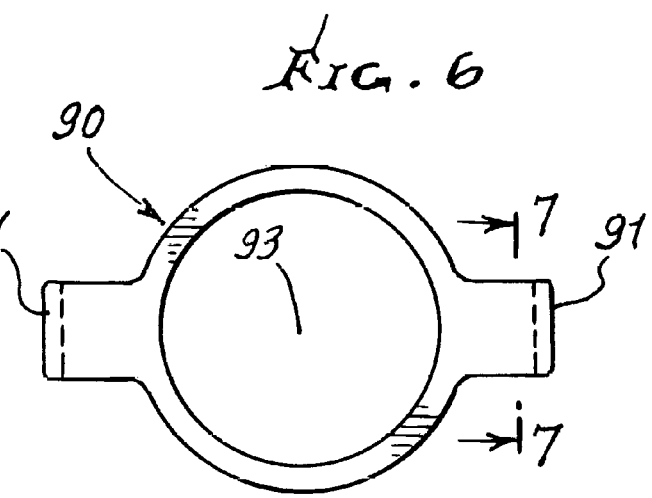
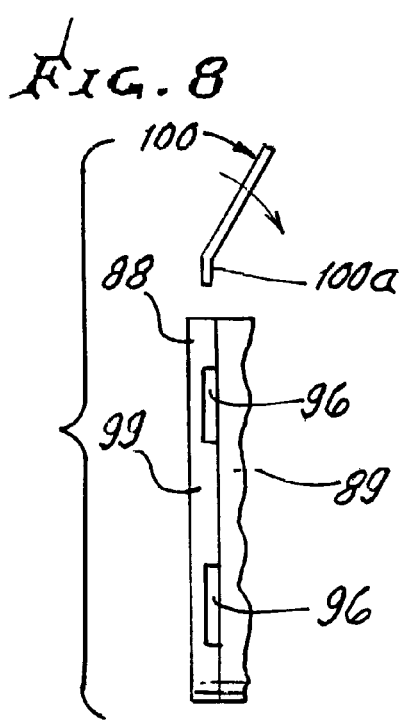
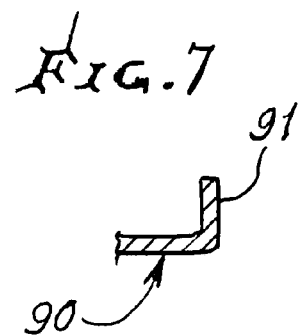

SEPARATION OF HIP JOINT LINER AND SOCKET ELEMENTS

BACKGROUND OF THE INVENTION

This invention relates generally to hip joints and freeing of attachment elements thereof, and more particularly concerns freeing of hip joint liners from sockets to which they have become attached, over time.

There is need for a safe, easily and quickly performed method of freeing a hip joint liner from a socket to which it has become attached. This is particularly needed where metallic surfaces of the liner and socket have become attached, as for example after extensive rubbing or frictional contact. There is particular need for the method and apparatus as defined herein.

SUMMARY OF THE INVENTION

It is a major object of the invention to provide improved method and apparatus meeting the above needs. Basically, the method of the invention for removing a hip socket liner from surface attachments to a socket, includes:

a) providing a carrier and multiple indentors or penetrators carried to be displaced relative to the carrier, b) applying the carrier to the liner so that the penetrators project toward a liner cup-shaped inner surface, c) effecting controlled and limited forceful displacement of the indentors or penetrators so that tips defined by the indentors or penetrators penetrate said liner cup-shaped surface, d) and transmitting jarring force to one of the liner and carrier whereby the liner is suddenly freed from said attachment to the socket. The freed liner is then withdrawn relative to the socket.

The cup-shaped interior surface is metallic, and outer surface attachment is spaced from said cup-shaped surface. At least three tips are typically employed (to penetrate directionally substantially normal to the cup-shaped liner surface.

A further object is to provide means to pull the carrier away from the liner to drag the liner, via the tips, free of engagement with the socket.

A further object is to provide axial force, and/or prying force, and/or vibration to assist liner extraction.

These and other objects and advantages of the invention, as well as the details of an illustrative embodiment, will be more fully understood from the following specification and drawings, in which:

DRAWING DESCRIPTION

FIG. 3 is a view like FIG. 2, but showing axial forcible detachment of the liner by axial displacement of the carrier and tips, directionally away from the acetabulum socket; and FIG. 4 is a section showing position of penetrator tip penetration into the liner.

FIG. 5 is a view like FIG. 3, but showing provision and use of means to push the liner free of the socket;

FIG. 6 is a plan view of a bracket useful in such pushing;

FIG. 7 is a view taken on lines 7-7 of FIG. 6; and

FIG. 8 is an edge view of under-cut structure facilitating prying and pushing apart of the liner and socket.

DETAILED DESCRIPTION

Figure 1:
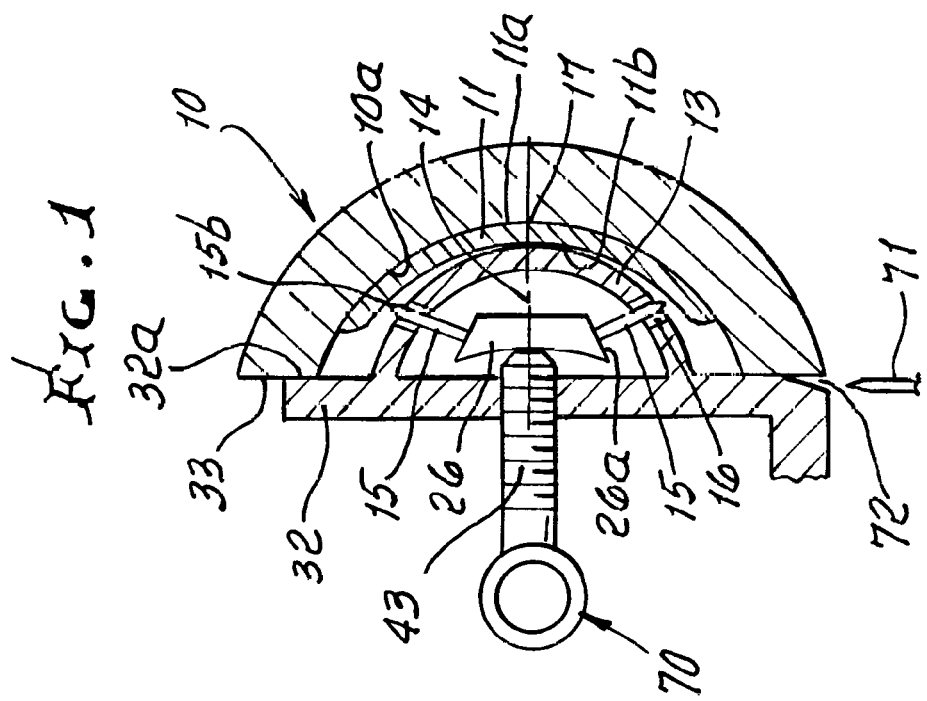
FIG. 1 is a section taken through a cup-shaped acetabulum having a liner to be detached from the cup socket, and a carrier for penetration, received in the cup.

In FIG. 1, a generally hemispherical acetabulum 10 has an inner cup-shaped surface 10*a*. A liner 11 fits in the acetabulum, and has an outer convex ball shaped surface 11*a* that becomes attached, over time, to the surface 10*a*. During hip replacement surgery, it becomes necessary to remove liner 11, which is difficult and prevents many problems.

In accordance with the invention, a carrier 13 is provided and sized to be axially received or inserted closely within the space surrounded by the liner interior cup-shaped surface 11*b*. The common axis shown at 14. Multiple penetrators 15 (at least three, but up to six) are carried by 13, within generally radial through openings 16 in the carrier. Those penetrators have shafts 15*a* movable endwise in the openings 16, and shaped tips 15*b* which are sharp, and presented toward the liner interior surface 11*b*, at spaced locations about axis 14. Those locations are preferably equally spaced about axis 14. At that time, the carrier may endwise engage the liner, as at axial location 17.

Figure 2:
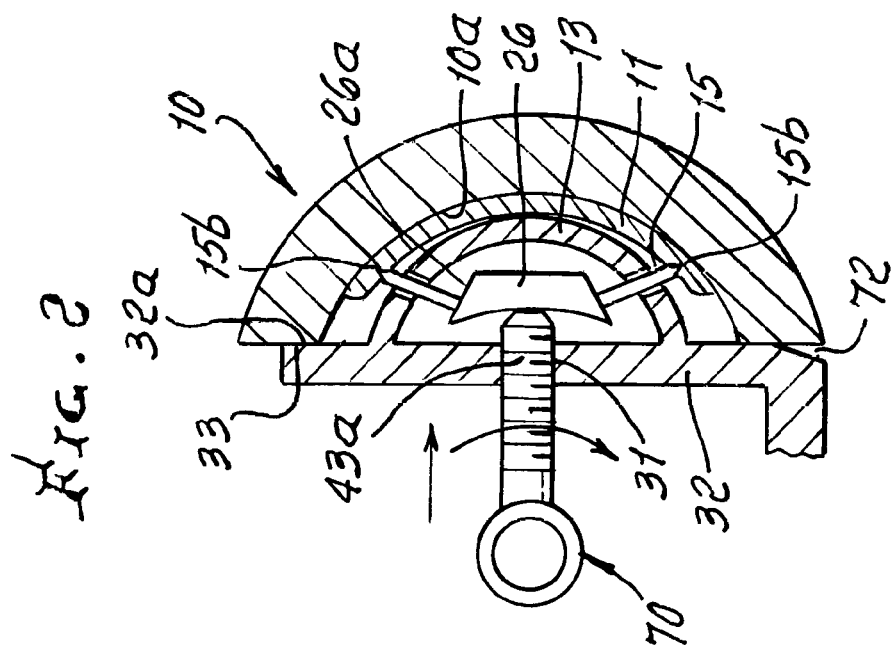
FIG. 2 is a view like FIG. 1, showing forcible displacement of the indentors or penetrators to push the tips into the liner inner surface.

Means is provided for effecting controlled limited forceful outward displacement of the indentors, so that their sharp tips are displaced toward and into the material of the liner cup-shaped surface 11*b*. The tips typically consist of non-bending material such as hard metal or diamond, and harder than the liner material, which may also be metallic, or consist of polyethylene or ceramic material to enable limited tip penetration or indentation into the liner. This condition is shown in FIG. 2 and also FIG. 4. Such displacement is typically effected by penetrator shaft end engagement with the outer tapered surface 26*a* of a cam 26, that surface being tapered conical, as shown. The cam is carried by a threaded shaft 43 to be rotated as indicated by arrow 30. The shaft threading 43*a* may engage the bore threads at 31 of a carrier wall 32. That wall may also engage the rim 33 of the acetabulum shell part, as shown at 32*a*, to position the cam.

As the penetrators are forced outward, they penetrate the liner as at grip locations 34, see in FIG. 4, which are located at equal spacing 35*a* about axis 14. Typically penetration is between 1/64 and 1/8 inch.

Thereafter, the carrier is forcibly pulled or displaced to the left, as in FIG. 3, which effects simultaneous leftward bodily displacement of the penetrators, their tapered tips, and the liner 11 gripped by the tips. Subsequently the shaft 43 is rotated in the opposite direction, to allow inward bodily displacement of the penetrators and tips, freeing the liner from the carrier. The acetabulum may be held in position, as by a holder 60, during such extraction of the liner. The penetrator tips are tapered so as to release from the liner as the cam 26 is displaced by shaft 43 rotation, as referred to. If desired, the assembly can be vibrated, as by tuning fork high frequency vibrator means so to assist jarring loose of the liner.

FIG. 1 also shows a puller hook 70 attached to the shaft 43, to be pulled to assist forcible extraction of the liner from the acetabulum. Alternatively, a prying tool or blade 71 may be inserted into a notch 72 between the acetabulum and carrier, and twisted, to assist liner extraction.

Referring to FIG. 5, it shows provision of means for transmitting pushing force acting between the carrier 13 and the hip socket 10 whereby the liner 11 is suddenly and/or forcibly freed from attachment to the socket. As shown, a pusher 80, when rotated pushes the carrier to the left, in the direction of arrow 81, whereby the pusher has operative connection to the carrier. Such a connection is shown in the form of a threaded connection 82, typically made up after the carrier has been connected to the liner by rotation of screw 43 to effect carrier displacement of the penetrators 15 into the liner, at the tips of the penetrators.

A nut 84 has external thread 85 that is made up into internal thread 86 on the carrier annular part 87, to make up connector 82. This causes the pusher to initially move to the right until it is stopped by engagement with the end 88a of spacer 88 engaging the socket, as at 89. Alternatively a bracket 90 may be assembled against the socket end 89, in position to block rightward travel of the nut. Continued rotation of the nut then causes the internal thread 86 on the carrier, and the carrier itself, to move bodily leftwardly, pushing the liner free of the socket, or free of an insert liner 92 carried by the socket, as in the case of a metal-to-metal ball joint where the liners 92 and 11 are "frozen" together.

Note that the nut 84 may have an end opening at 84a, providing access to the turning knob 70a on the stem carrying the cam 26.

It will therefore be seen that the invention provides means for readily removing a liner "frozen" in position in a socket, obviating need for the surgeon to repeatedly hammer a tool against the liner in an attempt to free it. Such hammer impacts can cause severe damage to the socket structure, and the present invention precludes risk of such potential damage.

FIG. 6 shows bracket 90 having turned ends or fittings 91 at opposite sides of axis 93 to fit against the socket ends, when the bracket interior annulus 90 is assembled over the carrier part 87. The bracket then transmits pressure from nut 84 to the socket end 89.

FIG. 8 shows provision of multiple (typically six) under cut openings 96 formed in the periphery of spacer 88, or in the bracket loop 99, adjacent end 89, to enable insert of the tip 100a of a pry tool or bar 100. Pivoting of bar 100 then enables tip 100a to pry or push the spacer 88 and liner free of the socket. A vibrating tuning fork may be used in place of bar 100.

Multiple under cuts enable selective and successive insertion of tip 100a in two or more under cuts, and prying at such multiple locations, to ensure liner release.

I claim:

1. An apparatus for removing a hip liner from a hip shell to which the hip liner is attached, comprising
   a) a carrier comprising a base and a convex dome projecting from a first surface of said base, said convex dome being configured to be received into a cup-shaped recess defined by a cup-shaped surface of the hip liner, said base comprising a through bore including internal threads and extending through the base, and said convex dome comprising an interior cavity and multiple through openings extending radially through the convex dome to communicate the interior cavity with an exterior of the convex dome,
   b) multiple movable penetrators carried by the carrier, each of said multiple penetrators consist of a force transmitting diverging elongated shaft, said elongated shaft extending longitudinally from a first end to an opposite second end remote from the first end, wherein the second end of the shaft being a free end and includes a sharp tip, said sharp tip being in endwise linear alignment with a main extent of the elongated shaft,
   c) a cam member being carried in the interior cavity of the carrier, said cam member comprising a body having a tapered surface engaged with each of said first ends of said multiple movable penetrators for displacing the penetrators endwise through the radial through opening of the carrier so that each of said sharp tips of said multiple movable penetrators is configured to indent and penetrate into the cup-shaped surface of the liner, wherein said cam member is configured to transmit a push-in force endwise to said first end of each of the multiple penetrators for sliding said sharp tip of each of the multiple penetrators through said multiple radial through openings of the convex dome of the carrier to indent and penetrate into the cup-shaped surface of the hip liner,
   d) a threaded shaft including external threads and extending along a threaded shaft longitudinal axis from a distal end to a proximal end and through the through bore of the base of the carrier, said distal end of the threaded shaft being coupled to a proximal side of the cam member, said proximal side being wider than a distal side of the cam member, and said proximal end of the threaded shaft including a shaft turning knob, and wherein the external threads of the threaded shaft engage the internal threads of the through bore of the carrier, said threaded shaft being configured for pulling the carrier axially longitudinally away from the hip shell whereby the carrier, the multiple penetrators and the hip liner are displaced axially away from the hip shell, wherein threading and unthreading the threaded shaft into the threaded through bore of the carrier, by rotating the thread shaft into the threaded bore about the threaded shaft longitudinal axis in opposite directions, applies pushing and pulling forces on the elongated shafts of the multiple penetrators by the cam member to thereby slide the sharp tips of the elongated shafts away from or towards the convex dome of the carrier, wherein said elongated shafts of the multiple penetrators are divergently angled relative to the threaded shaft to transmit pulling force from said carrier to said hip liner via said sharp tips, the carrier at said multiple through radial openings sidewardly engaging the elongated shafts at locations therealong in spaced relation to said sharp tips and spaced from the elongated shaft first ends engaged by the cam member to transmit pulling force exertion to the elongated shafts, free of the cam member, and
   e) wherein said elongated shaft first ends are independently facing the tapered surface of the cam member for independently engaging the cam member at spaced locations and being endwise movable relative to the carrier during the push-in force exertion by the cam member, and said elongated shafts are movable relative to the cam member during pull out force exertion by the carrier on the liner,
   f) a bracket configured to engage the carrier and configured to engage spaced portions of the hip shell to transmit force between the carrier and hip shell, the bracket having end fittings configured to engage external surface portions of the shell,
   g) wherein said bracket includes a rotatably adjustable tubular nut including a threaded portion, and wherein the carrier includes a threaded wall structure projecting from a second surface of the base of the carrier opposite to the convex dome, configured to engage with the threaded portion of the tubular nut, such that the tubular nut is axially aligned with said cam member and manipulable to displace the carrier and hip liner axially and longitudinally relative to the hip shell upon threading and unthreading the threaded portions of the tubular nut and the carrier relative to one another, and
   h) wherein a proximal portion of the threaded shaft penetrates through said tubular nut and carries said shaft turning knob, said bracket limiting travel of the nut relative to the carrier.

2. The apparatus of claim 1, wherein the nut is located mid-way between said end fittings.

3. The apparatus of claim 1, wherein the tubular nut defines an axis of rotation, said bracket end fittings engageable with a surface defined by the hip shell, said end fittings disposed at opposite sides of said axis of rotation.

4. The apparatus of claim 3, wherein said multiple penetrators are disposed about and diverge away from said axis of rotation.

5. The apparatus of claim 1, wherein said hip shell and said liner consists of one of the following: a) metal b) polyethylene c) ceramic material.

\* \* \* \* \*